United States Patent
Chavali et al.

(10) Patent No.: US 12,137,651 B2
(45) Date of Patent: Nov. 12, 2024

(54) METHODS AND SYSTEMS FOR USE IN IMPLEMENTING RESOURCES IN PLANT BREEDING

(71) Applicant: MONSANTO TECHNOLOGY LLC, Saint Louis, MO (US)

(72) Inventors: Srinivas Phani Kumar Chavali, Chesterfield, MO (US); Sambarta Dasgupta, Saint Louis, MO (US); Qianni Dong, Chesterfield, MO (US); Humberto Ignacio Gutierrez Gaitan, Wildwood, MO (US); Anthony Paul Kovacs, Creve Coeur, MO (US); Jorge Luis Moran, O'Fallon, MO (US); Silvano Assanga Ocheya, York, NE (US); Benjamin Bruce Stewart-Brown, Ames, IA (US); Zi Wang, San Mateo, CA (US); Chong Yu, Wildwood, MO (US)

(73) Assignee: MONSANTO TECHNOLOGY LLC, Saint Louis, MO (US)

(*) Notice: Subject to any disclaimer, the term of this patent is extended or adjusted under 35 U.S.C. 154(b) by 0 days.

(21) Appl. No.: 18/109,146

(22) Filed: Feb. 13, 2023

(65) Prior Publication Data
US 2023/0180688 A1 Jun. 15, 2023

Related U.S. Application Data

(63) Continuation of application No. 16/823,154, filed on Mar. 18, 2020, now Pat. No. 11,576,316.
(Continued)

(51) Int. Cl.
*A01H 1/04* (2006.01)
*G06N 3/126* (2023.01)

(52) U.S. Cl.
CPC ............... *A01H 1/04* (2013.01); *G06N 3/126* (2013.01)

(58) Field of Classification Search
CPC ............ A01H 1/04; A01H 1/02; G06N 3/126
See application file for complete search history.

(56) References Cited

U.S. PATENT DOCUMENTS

| | | |
|---|---|---|
| 10,327,400 B2 | 6/2019 | Chavali et al. |
| 11,576,316 B2 | 2/2023 | Chavali et al. |

(Continued)

FOREIGN PATENT DOCUMENTS

| | | |
|---|---|---|
| EP | 2399214 | 9/2019 |
| WO | WO2017/214445 | 12/2017 |

(Continued)

OTHER PUBLICATIONS

Hickey, John M. et al: "Evaluation valuation of Genomic Selection Training Population Designs and Genotyping Strategies in Plant Breeding Programs Using Simulation", Crop Science, vol. 54, No. 4, Jul. 1, 2014 (13 pages).

(Continued)

*Primary Examiner* — Manuel A Rivera Vargas
(74) *Attorney, Agent, or Firm* — Harness, Dickey & Pierce, P.L.C.

(57) ABSTRACT

Exemplary systems and methods are disclosed for allocating resources in a breeding pipeline to multiple origins. One exemplary method includes accessing a data structure including data representative of multiple origins, in which the data includes, for each of the multiple origins, a trait performance expression or genotypic component information. The exemplary method further includes determining a resource allocation, which allocates n resources among the multiple origins based on a probability associated with the trait performance expressions and/or the genotypic compo- (Continued)

nents for the origins, and then allocating the n resources in the breeding pipeline for the multiple origins, based on the determined resource allocation.

22 Claims, 4 Drawing Sheets

Related U.S. Application Data

(60) Provisional application No. 62/825,513, filed on Mar. 28, 2019.

(56) References Cited

U.S. PATENT DOCUMENTS

| | | | |
|---|---|---|---|
| 2008/0163824 | A1 | 7/2008 | Moser et al. |
| 2009/0031438 | A1* | 1/2009 | Kennard ............ C12N 15/8254 435/6.12 |
| 2009/0064360 | A1 | 3/2009 | Kerns et al. |
| 2011/0010102 | A1* | 1/2011 | Tao ...................... C12Q 1/6895 536/23.1 |
| 2012/0060233 | A1 | 3/2012 | Kennard et al. |
| 2015/0089691 | A1 | 3/2015 | Guo et al. |
| 2015/0181822 | A1* | 7/2015 | Daetwyler ............... A01H 1/08 506/9 |
| 2016/0024519 | A1 | 1/2016 | Kerns et al. |
| 2016/0132635 | A1 | 5/2016 | Buntjer et al. |
| 2017/0245446 | A1 | 8/2017 | Cooper et al. |
| 2017/0354105 | A1* | 12/2017 | Polavarapu ............ G06N 7/01 |
| 2017/0359978 | A1 | 12/2017 | Technow et al. |
| 2019/0000024 | A1 | 1/2019 | Rudolf Pilih et al. |
| 2019/0174691 | A1 | 6/2019 | Chavali et al. |
| 2019/0180845 | A1* | 6/2019 | Chavali ................... A01H 1/02 |
| 2019/0313591 | A1 | 10/2019 | Chavali et al. |
| 2020/0305373 | A1 | 10/2020 | Chavali et al. |
| 2022/0174900 | A1 | 6/2022 | Chavali et al. |

FOREIGN PATENT DOCUMENTS

| | | |
|---|---|---|
| WO | WO2019/113468 | 6/2019 |
| WO | WO2019/113480 | 6/2019 |

OTHER PUBLICATIONS

Aaron J. Lorenz: "Resource Allocation for Maximizing Prediction Accuracy and Genetic Gain of Genomic Selection in Plant Breeding: A Simulation Experiment", Genes|Genomes|Genetics. Vol. 3, No. 3, Mar. 1, 2013 (11 Pages).

Norman Adam et al: "Increased genomic prediction accuracy in wheat breeding using a large Australian panel", Theoretical and Applied Genetics, vol. 130, No. 12, Sep. 8, 2017 (13 pages).

Fenni Kang: "Plant growth models and methodologies adapted to their parameterization for the analysis of phenotypes", PhD Thesis, May 28, 2013 (179 pages).

Akdemir, D., 2016. Efficient breeding by genomic mating. Frontiers in genetics, vol. 7, p. 210.

Black F, L. R., 1992. Global portfolio optimization. Financial analysts journal, 48(5), pp. 28-43.

Fernández, J. T. M. a. C. A., 2001. Practical implementation of optimal management strategies in conservation programmes: a mate selection method. Animal biodiversity and conservation, 2(24), pp. 17-24.

Gorjanc, G. a. H. J., 2018. AlphaMate: a program for optimising selection, maintenance of diversity, and mate allocation in breeding programs. bioRxiv, p. 250837.

* cited by examiner

METHODS AND SYSTEMS FOR USE IN IMPLEMENTING RESOURCES IN PLANT BREEDING

CROSS-REFERENCE TO RELATED APPLICATION

This application is a continuation of U.S. patent application Ser. No. 16/823,154, filed on Mar. 18, 2020, which claims the benefit of and priority to U.S. Provisional Application No. 62/825,513, filed on Mar. 28, 2019. The entire disclosure of each of the above applications is incorporated herein by reference.

FIELD

The present disclosure generally relates to methods and systems for use in implementing resources in plant breeding, and, in particular, to methods and systems for use in allocating resources, in plant breeding settings, whereby the allocation is based on performance and/or genetic distributions of origins.

BACKGROUND

This section provides background information related to the present disclosure which is not necessarily prior art.

In plant development, modifications are often made in the plants either through selective breeding or genetic manipulation. Based on the particular selection or manipulation, the resulting plant material is introduced into a breeding pipeline, where plants are then created, grown, and tested. When performance of the plants is at or above an expected threshold, or at a highest performance, for example, for a given phenotype, or where frequencies of genotypes are at or above a certain threshold, η or example, etc., the plants may be considered target plants for advancement to further development and/or commercial implementation.

DRAWINGS

The drawings described herein are for illustrative purposes only of selected embodiments, are not all possible implementations, and are not intended to limit the scope of the present disclosure.

Corresponding reference numerals indicate corresponding parts throughout the several views of the drawings.

DETAILED DESCRIPTION

Figure 1:
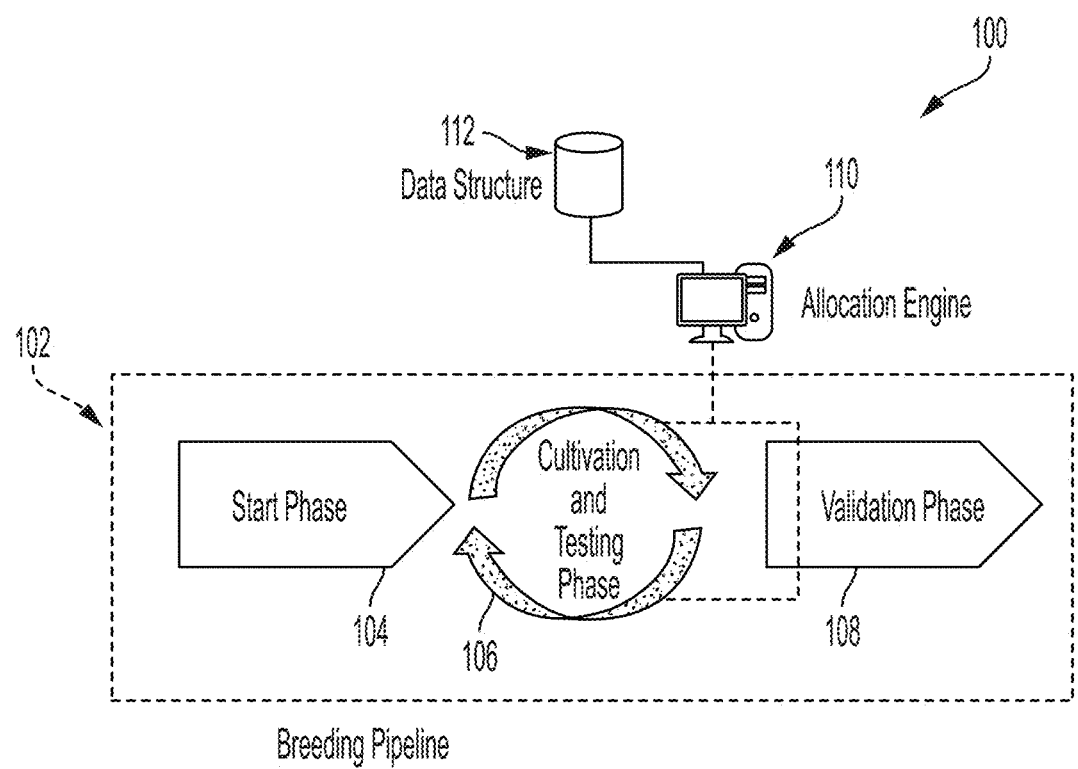
FIG. 1 is an exemplary system of the present disclosure suitable for allocating resources within plant breeding pipelines based, at least in part, on phenotypic and/or genotypic information.

Exemplary embodiments will now be described more fully with reference to the accompanying drawings. The description and specific examples included herein are intended for purposes of illustration only and are not intended to limit the scope of the present disclosure.

Various breeding techniques are commonly employed in agricultural industries to produce desired plants. For each of the techniques, and each of the processes associated with the techniques, resources are used, whether in creating plant materials, growing plant materials, or testing plant materials. Some such resources, as included in a plant breeding pipeline, include, but are not limited to, land such as field rows and field plots, greenhouse spaces, genotyping laboratory units, and doubled haploid units (DHUs). For example, when a certain number of origins are selected to undergo a doubled haploid (DH) process, the capacity of that process, which is dictated by whatever field, laboratory, man power, money, etc., or other resources, are required to run that process, may be broken into individual units, in this case DHUs, and then evenly distributed among the selected origins. In the case where 200 origins are selected and 1,000 DHUs are available, for instance, if the DHU resources are divided among them, each origin is allocated 5 DHUs. However, this even distribution does not account for any variation in the potential value of or potential genetic/phenotypic variation within the different origins.

Uniquely, the methods and systems herein allocate the resources within a breeding pipeline based on one or multiple phenotypic and/or genotypic features of the origins. In particular, a decision engine employs an algorithm, which accounts for probabilities of trait performance for the origins (e.g., expressed as a binomial distribution, etc.), as well as risk and/or genotypic components and/or diversity associated with the cohort of selected origins. By this algorithm, the available resources for the breeding process are allocated among the origins, with more resources devoted to origins with a higher likelihood of producing progenies performing above one or more thresholds and/or a higher likelihood of producing progenies expressing certain genetic components at rates deemed to be appropriate and/or desired for the breeding pipeline. In this manner, the breeding pipeline is improved (as a practical application of the methods and systems herein) by allocating resources more efficiently, to produce high performing and/or more genetically appropriate progenies.

With that said, progenies are generally organisms which descend from crosses between one or more parent organisms of the same species, i.e., origins. Progenies may refer to, for example, a universe of all possible progenies from a particular breeding program, a subset of all possible progenies specific to one or more origins, all offspring from one origin in a given generation, certain offspring from an origin, etc. Further, as used herein, the term "origin" refers to the set of parent(s) of progeny, and is therefore interpreted as either singular or plural, as applicable. The phenotypic data, trait distribution, ancestry, genetic sequence, commercial success, and additional information about the progenies are generally known and may be stored in memory described herein.

"Phenotypic data" as used herein includes, but is not limited to, information regarding the phenotype of a given progeny (e.g., a plant, etc.) or a population of progenies (e.g., a group of plants, etc.). Phenotypic data may include the size and/or heartiness of the progeny (e.g., plant height, stalk girth, stalk strength, etc.), yield, time to maturity, resistance to biotic stress (e.g., disease or pest resistance, etc.), resistance to abiotic stress (e.g., drought or salinity resistance, etc.), growing climate, or any additional phenotypes, and/or combinations thereof.

It should be appreciated that the methods and systems herein generally involve the phenotypic data associated with one or more origins, progenies, etc., and related phenotypic variances. That said, it should be appreciated that genotypic data may be used, in place of, in connection with, or in combination with the phenotypic data described herein (or otherwise) (e.g., to further supplement the phenotypic data and/or to further inform the models, algorithms, and/or predictions herein, etc.), in one or more exemplary implementations, to aid in the selection of groups of progenies and/or identification of sets of progenies consistent with the description herein. This may take the form of using an algorithm, for example, to predict phenotypic values and/or variances for a given cross from the genotypic data associated with that cross.

FIG. 1 illustrates an exemplary system 100 for allocating resources within plant breeding pipelines based, at least in part, on phenotypic and/or genotypic information, and in which one or more aspects of the present disclosure may be implemented. Although, in the described embodiment, parts of the system 100 are presented in one arrangement, other embodiments may include the same or different parts arranged otherwise depending, for example, on available resources for allocation to progenies, numbers of origins, particular types of origins, particular types of progenies, genotypes of interest, and/or phenotypes of interest, etc.

As shown in FIG. 1, the system 100 generally includes a breeding pipeline 102, which is provided to advance origins, progenies etc., through testing and selection, to further development and/or commercial use. The breeding pipeline 102, in general, defines a pyramidal progression, whereby a large number of potential origins are input and then successively reduced (e.g., selected down, etc.) to a preferred or desired number of origins, progenies, or plants. While the breeding pipeline 102 is configured to allocate resources therein, as provided herein, the breeding pipeline 102 may be configured to employ one or more other techniques which, may include a wide range of methods known in the art to create, select, or advance origins or progenies within the breeding pipeline 102, often depending on the particular plant and/or organism for which the breeding pipeline 102 is provided.

In certain breeding pipeline embodiments (e.g., large industrial breeding pipelines, etc.), testing, selections, and/or advancement decisions may be directed to hundreds, thousands, or more origins, progenies, etc., in multiple phases and at several locations over several years to arrive at a reduced set of origins, progenies, etc., which are then selected for commercial product development. In short, the illustrated breeding pipeline 102 is configured, by the testing, selections, etc., included therein, to reduce a large number of origins, progenies, etc., down to a relatively few number of superior-performing commercial products.

In this exemplary embodiment, the breeding pipeline 102 may be described with reference to, and is generally directed to, corn or maize and traits and/or characteristics thereof. However, it should be appreciated that the systems and methods disclosed herein are not limited to corn and may be employed in a plant breeding pipeline/program relating to other plants, for example, to improve any fruits, vegetables, grasses, trees, or ornamental crops, including, but not limited to, maize (*Zea mays*), soybean (*Glycine max*), cotton (*Gossypium hirsutum*), peanut (*Arachis hypogaea*), barley (*Hordeum vulgare*); oats (*Avena sativa*); orchard grass (*Dactylis glomerata*); rice (*Oryza sativa*, including indica and japonica varieties); sorghum (*Sorghum bicolor*); sugar cane (*Saccharum sp*); tall fescue (*Festuca arundinacea*); turf-grass species (e.g., species: *Agrostis stolonifera, Poa pratensis, Stenotaphrum secundatum*, etc.); wheat (*Triticum aestivum*), and alfalfa (*Medicago sativa*), members of the genus *Brassica*, including broccoli, cabbage, cauliflower, canola, and rapeseed, carrot, Chinese cabbage, cucumber, dry bean, eggplant, fennel, garden beans, gourd, leek, lettuce, melon, okra, onion, pea, pepper, pumpkin, radish, spinach, squash, sweet corn, tomato, watermelon, honeydew melon, cantaloupe and other melons, banana, castorbean, coconut, coffee, cucumber, Poplar, Southern pine, *Radiata* pine, Douglas Fir, *Eucalyptus*, apple and other tree species, orange, grapefruit, lemon, lime and other citrus, clover, linseed, olive, palm, *Capsicum, Piper*, and *Pimenta* peppers, sugarbeet, sunflower, sweetgum, tea, tobacco, and other fruit, vegetable, tuber, and root crops. The methods and systems herein may also be used in conjunction with non-crop species, especially those used as model methods and/or systems, such as *Arabidopsis*. What's more, the methods and systems disclosed herein may be employed beyond plants, for example, for use in animal breeding programs, or other non-plant and/or non-crop breeding programs.

As shown in FIG. 1, the breeding pipeline 102 includes an origin start phase 104 and a cultivation and testing phase 106, which together identify and/or select one or multiple origins or progenies for advancement to a validation phase 108. In the validation phase 108, then, the progenies are introduced into pre-commercial testing as progenies, lines, or as hybrids, for example, depending on the particular type of progenies, or other suitable processes (e.g., a characterization and/or commercial development phase, etc.) with an end goal and/or target to be planting and/or commercializing the progenies. With that said, it should be appreciated that the breeding pipeline 102 may include a variety of conventional processes known to those skilled in the art in the three different phases 104, 106, and 108 illustrated in FIG. 1.

In the origin start phase 104, a pool of potential origins is reduced to a selected set of origins, for example, based on origin selection systems and/or based (at least in part) on the methods and systems disclosed in Applicant's co-owned U.S. patent application Ser. No. 15/618,023, titled "Methods for Identifying Crosses for use in Plant Breeding," the entire disclosure of which is incorporated herein by reference. It should be appreciated that other selection techniques may be employed to select origins in the origin start phase 104, which may be based on a variety of data associated with the origins and/or predictions about the origins, etc.

Once the origins are selected, the selected origins are directed to the cultivation and testing phase 106, in which the progenies are planted or otherwise introduced into one or more growing spaces, such as, for example, greenhouses, shade houses, nurseries, breeding plots, fields (or test fields), etc. As should be understood, the cultivation and testing phase 106 includes an amount of resources to grow and test the progenies of the selected origins. The resources may include, for example, double haploid units, or DHU's, which are the resources required to grow and test the progeny of the origins. It should be appreciated that other resources may be included in the cultivation and testing phase 106, and subject to the techniques explained herein. Here, the resources within the cultivation and testing phase 106 are, in general, allocated by an allocation engine 110, to the origin pairs identified in the selected origins, as described below.

Once the progenies are grown in the cultivation and testing phase 106, each is tested (again as part of the cultivation and testing phase 106 in this example) to derive and/or collect phenotypic and/or genotypic data for the progeny, whereby the phenotypic and/or genotypic data are stored in one or more data structures. Common examples of phenotypes that may be assessed through such testing include, without limitation, disease resistance, abiotic stress resistance, yield, seed and/or flower color, moisture, size, shape, surface area, volume, mass, and/or quantity of chemicals in at least one tissue of the seed, for example, anthocyanins, proteins, lipids, carbohydrates, etc., in the embryo, endosperm or other seed tissues. As an example, where a progeny (e.g., cultivated from a seed, etc.) has been selected or otherwise modified to produce a particular chemical (e.g., a pharmaceutical, a toxin, a fragrance, etc.), the progeny can be assayed to quantify the desired chemical.

When the progeny are considered successes, based on the phenotypic and/or genotypic data and a variety of thresholds and/or bases, the progeny are advanced to the validation phase 108, in which the progenies are exposed to pre-commercial testing or other suitable processes (e.g., a characterization and/or commercial development phase thereof, etc.) with a goal and/or target to be planting and/or commercialization of the progenies. That is, the set of progenies may then be subjected to one or more additional/further tests and/or selection methods, trait integration operations, hybridization with other inbred lines, and/or bulking techniques to prepare the progenies, or plant material based thereon, for further testing and/or commercial activities.

Referring again to the allocation of resources, and with continued reference to FIG. 1, the allocation engine 110 includes (and/or is associated with) at least one computing device, which may be a standalone computing service, or may be a computing device integrated with one or more other computing devices. The allocation engine 110 is configured, then, by computer-executable instructions and/or one or more algorithms provided herein (or variants thereof or others), to perform the operations described herein, for example, as part of allocating resources in the breeding pipeline 102.

In addition, the system 100 further includes an origins data structure 112 coupled to the allocation engine 110. In this exemplary embodiment, the origins data structure 112 includes data related to the origins and, further, ancestors and/or related origins, progenies, etc. The data may include various types of data for the progenies, origins, etc., related, for example, to the origin of the plant material, testing of the plant material, etc. One example type of data included in the data structure 112 is genetic marker data for the origins, which extends back two years, three years, five years, six years, ten years, or more, etc. More generally, the data structure 112 may include data consistent with a present growing/testing cycle and may include data related to prior growing/testing cycles. For example, the data structure 112 may include data indicative of various different characteristics and/or traits of the plants for the current and/or the last one, two, five, ten, fifteen, or more or less years of the plants through the cultivation and testing phase 106, or other growing spaces included in or outside the breeding pipeline 102, and also present data from the cultivation and testing phase 106.

In general, the origins data structure 112 includes phenotypic data, which have been measured, simulated, or both, for the origins, with which phenotypic variances for each origin may be generated.

Figure 2:
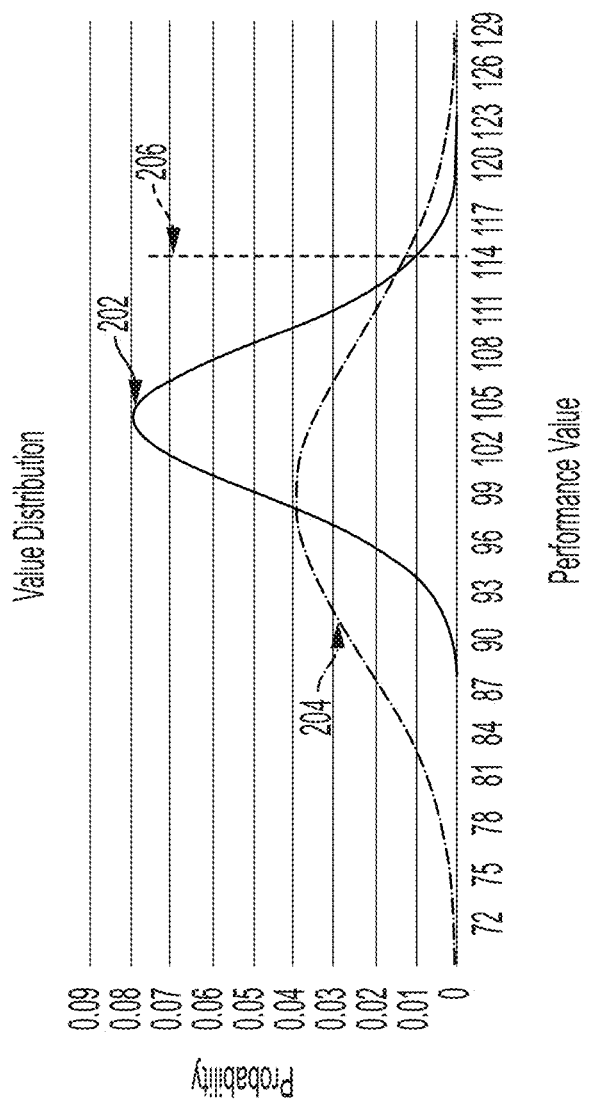
FIG. 2 is an exemplary graphic of trait performance probability distributions for multiple origin pairs, and which form a basis for the resource allocation in the system of FIG. 1.

An example such variance is illustrated in FIG. 2. Curve 202 represents the phenotypic variance of a first origin pair and curve 204 represents the phenotypic variance of a different second origin pair. In this example, the first origin pair includes a low bi-paternal genetic similarity among the included parents, so that the combination, in general, will produce a diverse set of progenies based on the number of loci where recombination could happen. Conversely, the second origin pair includes a relatively high bi-parental similarity between its parents, so that the combination, in general, will produce a less diverse set of progenies (by comparison to the former origin) based on a reduced number of loci where recombination could occur.

As shown in FIG. 2, the greater probability of producing a higher performing progeny is associated with the origin pair for the curve 202, as the curve includes a greater area under the curve at the right end, past performance threshold 206. In this example, a larger x-axis value indicates a higher performing progeny, and the fact that curve 202 has more area under the curve past the threshold 206 indicates that it has a greater likelihood of producing progeny in that performance region.

In this exemplary embodiment, the allocation engine 110 is configured to rely on the phenotypic variances, for a given set of origin pairs, to allocate the available resources for the breeding process among the origin pairs. Specifically, the allocation engine 110 is configured to employ the algorithm provided below, as Equation (1), and to minimize or reduce an output (across different permutations of resource allocations).

$$\text{minimize} \sum_{i=1}^{N} -\lambda_1 \mathbb{P}(\theta_i > \eta) x_i + \\ \lambda_2 [\mathbb{P}(\theta_i > \eta)(1 - \mathbb{P}(\theta_i > \eta)) U_i x_i] + \lambda_3 \|TI_H x - \xi\|_1 \quad (1)$$

The equation above is uniquely constructed to indicate resource allocation. It includes three main terms, which, respectively, include performance—$\lambda_1 \mathbb{P}(\theta_i > \eta) x_i$, risk $\lambda_2 [\mathbb{P}(\theta_i > \eta)(1 - \mathbb{P}(\theta_i > \eta)) U_i x_i]$, and diversity $\lambda_3 \|TI_H x - \xi\|_1$, where equation (1) is expected to be minimized or relatively minimized for a given set of origins. Each of the terms includes a weighting variable, $\lambda_1$, $\lambda_2$ and $\lambda_3$, which is determined based on either a decision marker's preference, mining through historical successes, machine learning methodologies, random chance, and/or any other appropriate method.

Apart from the weights, the first term of Equation (1) describes a probability that the performance of the breeding value for the i-th origin, $\theta_i$, will be greater than a target threshold, $\eta$. This is a probability distribution of trait performance and/or probability of expressing certain genetic components. For example, the term may represent the probability that progenies from origin $\theta_i$ demonstrate a yield greater than the desired yield threshold, $\eta_{YLD}$, or the probability that progenies from origin $\theta_i$ demonstrate a stalk standability greater than the desired stalk standability threshold, $\eta_{STLK}$. This may even apply to more apparently binary characteristics, such as the presence or absence of a specific haplotype, in which case the probability distribution may take a binomial form and the threshold, $\eta$, may take a more trivial role of indicating the binary outcomes.

Probability distributions of values of traits for two given populations (of origins) are represented, for example, in FIG. 2, as the two curves 202, 204 for the different origins, i.e., the first origin, or origin_1, which is referenced by curve 202, and the second origin, or origin_2, which is referenced by curve 204. The value is a potential distribution for progeny resulting from the specific origin, which is shown along with a corresponding probability of that value being demonstrated by any given progeny resulting from the origin, or, generally, a binomial distribution. For instance, the value along the x-axis could be any trait of interest, such as, for example, yield values, etc., and the values along the y-axis would be the probability density at the trait value given on the x-axis. With continued reference to FIG. 2, when the threshold or η is set to a value of 114, for example (as indicated by the dotted line reference 206), a probability of the origin having a value above the threshold is determined based on the illustrated curve. This is generally understood as the area under the curve(s) to the right of the threshold at the value of 114. The probability is then multiplied by $x_i$, which is the resources (e.g., number of DHUs, etc.) to be allocated to the i-th origin.

The second term of Equation (1) includes the risk associated with the allocation of resources to the i-th origin. In particular, the risk is again based on the probability that the breeding value for the i-th origin, $\theta_i$, will be greater than the target threshold, η. However, the probability in risk is included as the variance of the breeding value (i.e., $\mathbb{P} \times (1-\mathbb{P})$), as represented by the curve in FIG. 2, for example. This is multiplied, again, by $x_i$, which is the resources (e.g., number of DHUs, etc.) to be allocated to the i-th origin, which is further multiplied by $U_i$, which is the confidence level in the genotypic and phenotypic learning for the i-th origin. This confidence level, $U_i$, can be best understood as how much confidence can be given to the genotypic and phenotypic values and distributions attributed to the i-th origin (as shown in FIG. 2, for example) based on how much data have been collected about the i-th origin, how well represented the genetic background of the i-th origin is in any relevant training set, and the underlying confidence/error intervals for any analyses, predictive models, etc., involved in this process. The confidence level, $U_i$, provides a basis to quantify the risk associated with the allocation of resources(s) to the particular origin. Risk may further account for traits indicative of risk, such as, for example, stability, disease resistances, etc.

The third term of the Equation (1) includes a diversity of the origins included with the allocation of resources to the i-th origin. Specifically, a transition probability matrix from the progeny heterotic groups to the origin heterotic groups, T, is multiplied by an incidence matrix for mapping the origins heterotic groups to the origins, $I_H$, and the origins selected, x. This is then reduced by a target portfolio of breeding objective, ξ. In effect, then, the third term represents the selected origin's deviation from a target portfolio.

In the exemplary embodiment, Equation (1) is employed by the allocation engine 110, and constrained by several conditions. First, x is a positive integer, as indicated in Equation (2) below, and y, as used in the following equations, is an indicator of x, as indicated in Equation (3).

$$x \in \mathbb{Z} \quad (2)$$

$$y \in \{0, 1\} \quad (3)$$

The sum of x, which is the amount of resources assigned to each i-th origin, must be equal to n, which is a total number of resource units, e.g., DHUs, field plots, pots in a greenhouse, laboratory resources, etc., to be assigned, by Equation (4). Stated another way, when 1000 DHUs are provided to be allocated in Equation (1), each of the DHUs must be assigned to an origin. And, Equation (5) dictates that the sum of y must be equal to the total number of origins selected, m. That is, a group of origins is identified to Equation (1) for which resources are to be allocated, and Equation (1) must allocate at least one resource to each origin, so that each origin is represented in y.

$$1^T x = n \quad (4)$$

$$1^T y = m \quad (5)$$

In addition to the above, the Equation (6) imposes an upper limit, $u_{upper}$, and a lower limit, $u_{lower}$, on the number of resources allocated to an i-th origin, and Equation (7) imposes a limit on x and y, relative to the upper limit.

$$u_{lower} \leq x \leq u_{upper} \quad (6)$$

$$x/u_{upper} \leq y \leq x \quad (7)$$

Gender limitations are also imposed through Equations (8) and (9), as provided below. Specifically, a male incidence vector of the origins, M, which is summed for the allocated resources, y, must be greater than or equal to a number of origins elected, m, multiplied by a male gender threshold, $\alpha_M$, set by the breeder or otherwise. The threshold is set as a percentage, such as, for example, 40%, 60%, or a percentage therebetween, or another percentage, based on a status of the breeding pipeline 102 and/or a future target. Likewise, a female incidence vector of the origins, F, which is summed for the assigned resources, y, must be greater than or equal to a number of origins elected, m, multiplied by a female gender threshold, $\alpha_F$, set by the breeder or otherwise.

$$M^T y \geq m \alpha_M \quad (8)$$

$$F^T y \geq m \alpha_F \quad (9)$$

And, finally, in this exemplary embodiment, Equation (10) imposes a limit by the number of occurrences of parents, where a parent incidence vector of the origins, $I_p$, which is summed for the assigned resources, y, must be less than or equal to a number of origins elected, m, multiplied by a parent threshold, $\alpha_p$, as set by the breeder or otherwise. The parent threshold, $\alpha_p$, is set as a percentage, such as, for example, 5% or another percentage, based on a status of the breeding pipeline 102 or decision making preference, so as to ensure there is a desired and/or healthy amount of diversity in the breeding pipeline for future genetic gain.

$$I_p y \leq m \alpha_p \quad (10)$$

While described above in the context of the equations, the variable and/or terms included in Equations (1)-(10) are provided in Table 1, along with a definition of the variables and/or terms. It should be appreciated that the terms and variables are not strictly limited to the definitions below, but include any and all readily appreciable variances, as would be understood by those skilled in the art.

TABLE 1

| Term | Description |
| --- | --- |
| n | number of resource units |
| m | number of origins selected |
| η | target threshold for breeding value |
| $\theta_i$ | breeding value for i-th origin |
| $P_i$ | probability of breeding value larger than threshold for i-th origin |
| $U_i$ | confidence level of genetic learning for i-th origin |
| ξ | target portfolio of breeding objectives |
| $I_P$ | incidence matrix mapping parents to origins |
| $I_H$ | incidence matrix mapping origins heterotic groups to origins |
| T | transition probability matrix from progeny heterotic groups to origin heterotic groups |
| M | male incidence vector |
| F | female incidence vector |

TABLE 1-continued

| Term | Description |
|---|---|
| $x_i$ | amount of resource assigned to i-th origin |
| $y_i$ | binary decision, 1 if i-th origin is assigned with positive resource, else 0 |

The allocation engine 110 is configured to then solve the equations above, which in effect allocates resources, e.g., DHUs, etc., among the origins based on performance, risk and diversity. When the allocation engine 110 determines the allocation, the allocation engine 110 is further configured to output or transmit the allocation, per origin, to one or more breeders. In response, then the breeder(s), in the pipeline 102, employ the resource to the origins, as defined by the allocation provided from the allocation engine 110, thereby populating the breeding pipeline 102.

What's more, it should be appreciated that the allocation engine 110 may be configured to provide (e.g., generate and cause to be displayed at a computing device of a breeder, etc.) and/or respond to a user interface, through which a breeder (broadly, a user) is able to provide one or more inputs, which are then relied upon by the allocation engine 110, in making allocations of resources among origins. User interfaces may be provided to receive the inputs, directly at a computing device (e.g., computing device 300 as described below, etc.) associated with the breeder, in which the allocation engine 110 is employed, or via one or more network-based applications through which a remote user (again, potentially a breeder) may be able to interact with the allocation engine 110 (e.g., an application programming interface (API), etc.), etc.

Figure 3:
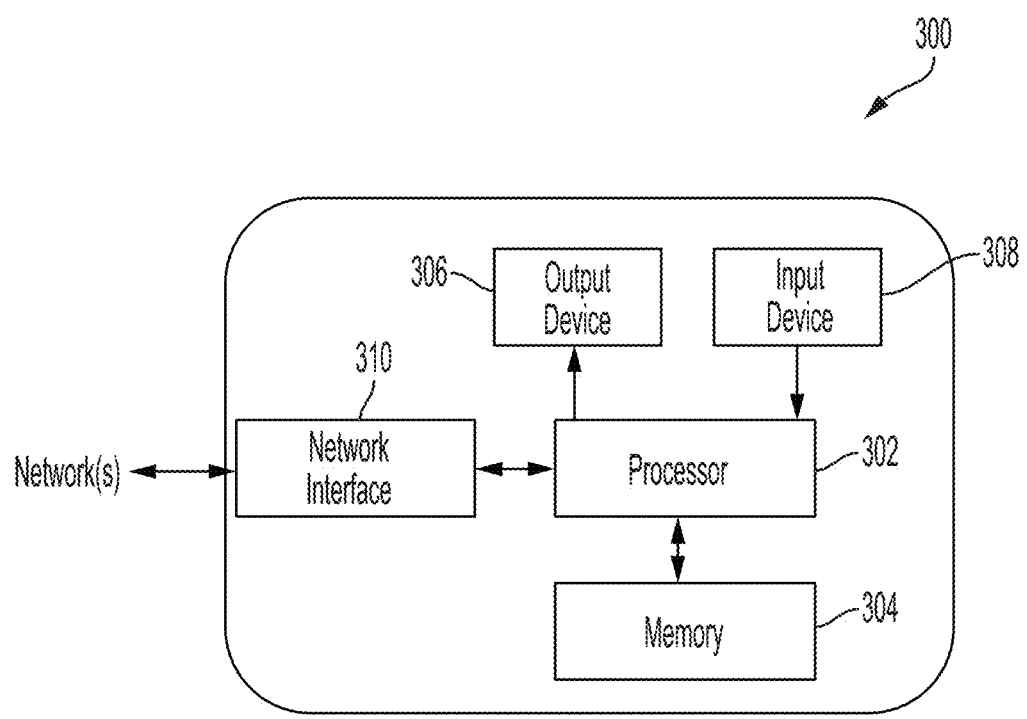
FIG. 3 is a block diagram of an exemplary computing device that may be used in the system of FIG. 1.

FIG. 3 illustrates an exemplary computing device 300 that may be used in the system 100, for example, in connection with various phases of the breeding pipeline 102, or in connection with the allocation engine 110 and/or the progeny data structure 112, etc. For example, at different parts of the breeding pipeline 102, breeders or other users interact with computing devices, consistent with computing device 300, to enter data and/or access data in the progeny data structure 112 to support breeding decisions and/or testing completed/accomplished by such breeders or other users. In connection therewith, the allocation engine 110 of the system 100 includes and/or is implemented in at least one computing device consistent with computing device 300. In connection therewith, the computing device 300 may be uniquely, or specifically, configured, by executable instructions, to implement the various algorithms and other operations described herein with regard to the allocation engine 110. It should be appreciated that the system 100, as described herein, may include a variety of different computing devices, either consistent with computing device 300 or different from computing device 300.

The exemplary computing device 300 may include, for example, one or more servers, workstations, personal computers, laptops, tablets, smartphones, other suitable computing devices, combinations thereof, etc. In addition, the computing device 300 may include a single computing device, or it may include multiple computing devices located in close proximity or distributed over a geographic region, and coupled to one another via one or more networks. Such networks may include, without limitations, the Internet, an intranet, a private or public local area network (LAN), wide area network (WAN), mobile network, telecommunication networks, combinations thereof, or other suitable network(s), etc. In one example, the progeny data structure 112 of the system 100 includes at least one server computing device, while the allocation engine 110 includes at least one separate computing device, which is coupled to the progeny data structure 112, directly and/or by one or more LANs, etc.

With that said, the illustrated computing device 300 includes a processor 302 and a memory 304 that is coupled to (and in communication with) the processor 302. The processor 302 may include, without limitation, one or more processing units (e.g., in a multi-core configuration, etc.), including a central processing unit (CPU), a microcontroller, a reduced instruction set computer (RISC) processor, an application specific integrated circuit (ASIC), a programmable logic device (PLD), a gate array, and/or any other circuit or processor capable of the functions described herein. The above listing is exemplary only, and thus is not intended to limit in any way the definition and/or meaning of processor.

The memory 304, as described herein, is one or more devices that enable information, such as executable instructions and/or other data, to be stored and retrieved. The memory 304 may include one or more computer-readable storage media, such as, without limitation, dynamic random access memory (DRAM), static random access memory (SRAM), read only memory (ROM), erasable programmable read only memory (EPROM), solid state devices, flash drives, CD-ROMs, thumb drives, tapes, hard disks, and/or any other type of volatile or nonvolatile physical or tangible computer-readable media. The memory 304 may be configured to store, without limitation, the progeny data structure 112, phenotypic data, testing data, origin data (e.g., trait performance distributions, etc.), weights, thresholds, and/or other types of data (and/or data structures) suitable for use as described herein, etc. In various embodiments, computer-executable instructions may be stored in the memory 304 for execution by the processor 302 to cause the processor 302 to perform one or more of the functions described herein, such that the memory 304 is a physical, tangible, and non-transitory computer-readable storage media. Such instructions often improve the efficiencies and/or performance of the processor 202 that is performing one or more of the various operations herein. It should be appreciated that the memory 304 may include a variety of different memories, each implemented in one or more of the functions or processes described herein.

In the exemplary embodiment, the computing device 300 also includes an output device 306 that is coupled to (and is in communication with) the processor 302. The output device 306 outputs, or presents, to a user of the computing device 300 (e.g., a breeder, etc.) by, for example, displaying and/or otherwise outputting information such as, but not limited to, selected progeny, progeny as commercial products, and/or any other types of data as desired. It should be further appreciated that, in some embodiments, the output device 306 may comprise a display device such that various interfaces (e.g., applications (network-based or otherwise), etc.) may be displayed at computing device 300, and in particular at the display device, to display such information and data, etc. And in some examples, the computing device 300 may cause the interfaces to be displayed at a display device of another computing device, including, for example, a server hosting a website having multiple webpages, or interacting with a web application employed at the other computing device, etc. Output device 306 may include, without limitation, a liquid crystal display (LCD), a light-emitting diode (LED) display, an organic LED (OLED)

display, an "electronic ink" display, combinations thereof, etc. In some embodiments, output device 306 may include multiple units.

The computing device 300 further includes an input device 308 that receives input from the user. The input device 308 is coupled to (and is in communication with) the processor 302 and may include, for example, a keyboard, a pointing device, a mouse, a stylus, a touch sensitive panel (e.g., a touch pad or a touch screen, etc.), another computing device, and/or an audio input device. Further, in some exemplary embodiments, a touch screen, such as that included in a tablet or similar device, may perform as both output device 306 and input device 308. In at least one exemplary embodiment, the output device 306 and the input device 308 may be omitted.

In addition, the illustrated computing device 300 includes a network interface 310 coupled to (and in communication with) the processor 302 (and, in some embodiments, to the memory 304 as well). The network interface 310 may include, without limitation, a wired network adapter, a wireless network adapter, a telecommunications adapter, or other devices capable of communicating to one or more different networks. In at least one embodiment, the network interface 310 is employed to receive inputs to the computing device 300. For example, the network interface 310 may be coupled to (and in communication with) in-field data collection devices, in order to collect data for use as described herein. In some exemplary embodiments, the computing device 300 may include the processor 302 and one or more network interfaces incorporated into or with the processor 302.

Figure 4:
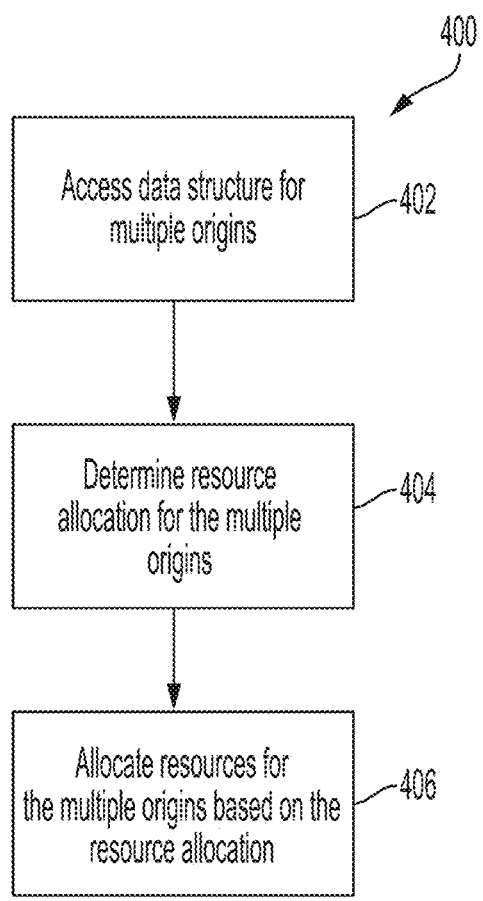
FIG. 4 is an exemplary method, suitable for use with the system of FIG. 1, for allocating resources within plant breeding pipelines based, at least in part, on phenotypic and/or genotypic information.

FIG. 4 illustrates an exemplary method 400 of selecting progenies in a progeny identification process. The exemplary method 400 is described herein in connection with the system 100, and may be implemented, in whole or in part, in the allocation engine 110 of the system 100. Further, for purposes of illustration, the exemplary method 400 is also described with reference to the distributions in FIG. 2 and the computing device 300 of FIG. 3. However, it should be appreciated that the method 400, or other methods described herein, are not limited to the system 100, the distributions in FIG. 2, or the computing device 300. And, conversely, the systems, data structures, and computing devices described herein are not limited to the exemplary method 400.

To begin, a breeder (or other user) initially identifies a plant type (e.g., maize, soybeans, etc.) and one or more desired phenotypes, potentially consistent with one or more desired characteristics and/or traits to be advanced in the identified plant, or a desired performance in a commercial plant product. In turn, based on the above and/or one or more other criteria, the breeder or user, alone or through various processes, selects multiple origins to be a starting point. The origin may be selected by any suitable means, in view of the above, including, again, via the methods described in Applicant's co-owned U.S. application Ser. No. 15/618,023, which is incorporated herein by reference in its entirety.

In this exemplary embodiment, 200 origins are selected, which may be referred to as "m," and the available resources include 1,000 DHUs, which may be referred to as "n." By way of explanation, these numbers may provide $1.323 \times 10^{215}$ different possible ways to distribute 1,000 DHUs among the 200 origins (where each origin is included in at least one DHU and is further permitted to be included up to a maximum number of the remaining resources).

For the selected multiple origins, the data structure 112 includes various data representative of the origins. Among the data, the data structure 112 includes a trait performance distribution, which, in general, provides a probability that the origin includes a specific value of a trait. The probability is generally determined based on testing and/or prediction models, for example, which are trained on historical data, including past genetic products and the distribution of the specific trait of interest. As shown in FIG. 2, for example, the trait performance distribution is illustrated as a binomial distribution of the two origins, at curves 202 and 204, which is indicative of a probability of the respective origins performing at the value indicated. So, for example, the first origin, or origin_1 (identified at curve 202), has a 0.08 probability of having a performance of 104, while the second origin, or origin_2 (identified at curve 204), has a 0.03 probability of having a performance of 107. As can be seen, in FIG. 2, the probability of performance above the exemplary target threshold 206 (having the performance value of 114) is greater for the second origin (or origin_2 identified at curve) 204), than for the first origin (or origin_1, identified at curve 202). It should be appreciated that a distribution and/or other expression of probability of the type described herein is included in the data structure 112 for each of the multiple selected origins.

In addition, the data structure 112 also includes a confidence level of genetic learning, which is referred to above as $U_i$. This confidence level can be based on the frequency at which genetic material similar to a given origin is present within sets previously tested in the breeding pipeline 102 and/or historical data sets used to train one or more suitable predictive models employed within the overall breeding process and/or the resource allocation process described herein. The confidence level further accounts for the robustness of the one or more predictive models employed, which may be based on, for example, how well the origin is known and/or confidence of the origin delivering on the distribution. Simply, this frequency may be used in comparison to the average frequency of genetic families within the training sets to create an estimation of how much more or less, confidence exists in the model. For instance, if a certain genetic family is represented 1.5× more often within the training set than the average family would be, 1.5 could be used as the confidence level for this particular line. Likewise, another family could be represented at 0.75×, and a cross between these two lines might be characterized with $U_i = 1.5 \times 0.75 = 1.125$ where the confidence level for the origin is a simple multiplication of the confidence levels in the parents. It is important to note that the genetic confidence may be derived in much more sophisticated manners as well. For instance, the confidence for each parent of the cross could be derived as a result of a Bayesian analysis of the entire germplasm pool. The subsequent origin confidence level could itself be derived using a more sophisticated convolution of the parental confidences, or, even more directly, could be derived from the confidence outputs of any machine learning algorithms and/or simulation engines that may have been used to evaluate this origin's expected breeding value variance.

Also, the data structure 112 includes a target portfolio for breeding objective sets, for example, by the breeder at the outset of the start phase 104 (or after), which is. The target portfolio may include any of a number of targets and distributions that define how a target, desired, or ideal germplasm pool in the breeding pipeline 102 may look. Some of these targets may include gender (heterotic pool) distributions across the breeding pipeline 102, the distribution of different germplasm clusters within the breeding pipeline 102, and the desired distribution of parents in different stages of the breeding lifecycle (e.g., to balance the use of old, proven parents with young, less proven parents with newer genetics; etc.). For one example profile, an operator may decide that a pipeline should have at least 45% male lines and 45% females lines, but that the remaining may be selected by performance, while at the same time, another operator may decide that the origins in the pipeline must be a perfect 50/50 split between male and female heterotic pools. In yet another example, a target profile may be based on the distribution of maturities of origins within a specific breeding pipeline. For instance, if a pipeline were responsible for a six day span of crop maturities, a potential target maturity profile for the material to be added to the pipeline may indicate that 25% of all origins should fall in the earliest 2 days of that span, 50% should fall in the middle two days, and 25% of origins should fall within the last two days of the span. Such a target profile would help to ensure that a majority of the lines produced by origins with such a mid-parent maturities (average of the two parents individual maturities) would fall within the six-day window of the pipeline. Notwithstanding these specific examples, it should be appreciated that the target profile may include any profile deemed desirable by a breeder and/or person associated with the allocation of resources among the origins included in the allocation.

Targets may be set in a number of ways. Most simply, targets may be set by human input to align the breeding pipeline 102 with certain business goals or limitations. These targets may be communicated to data scientists, and then manually transferred into the allocation engine 110, or they may be stored in a database or API through the use of a web-based user interface or other tool. With the development of more advanced analytics and simulations, the targets could be set algorithmically based on a plan, roadmap or strategy determined to have a desired and/or highest likelihood of improving, taking advantage of and/or maximizing the breeding pipeline 102 and/or business performance associated with the allocated resources, and, potentially, aligning closely with future market needs for a given plant, etc. The targets could be stored in a database or API for later retrieval by the allocation engine 110, as desired and/or required to perform as described herein.

As shown in FIG. 4, at 402 in the method 400, the allocation engine 110 accesses data included in the data structure 112 for the multiple selected origins. The data includes, for example, a probability distribution for trait performance for each of the selected origins. Other data, for each origin, may include gender data, parental and/or heterotic data, etc.

Then, the allocation engine 110 determines, at 404, a resource allocation of the available resources (i.e., the 1,000 DHUs in this example) for the multiple selected origins. In particular, in this exemplary embodiment, the allocation engine 110 employs the allocation algorithm of Equation (1) (reproduced below). It should be appreciated that, in other method embodiments, different algorithms (whether derived from Equation (1) or not) may be employed to allocate available resources among a set of origins.

$$\text{minimize} \sum_{i=1}^{N} -\lambda_1 \mathbb{P}(\theta_i > \eta) x_i +$$
$$\lambda_2 [\mathbb{P}(\theta_i > \eta)(1 - \mathbb{P}(\theta_i > \eta)) U_i x_i] + \lambda_3 \|TI_H x - \xi\|_1$$

As explained above, the algorithm of Equation (1) includes three terms, which relate, generally, to performance, risk and diversity.

It is important to note that the resource allocation process described herein can be applied not just to high-level decisions such as how to distribute DHUs or how to allocate testing plots but also to ancillary and sub-decisions as well. For instance, even once this process has been used to allocate DHUs, as discussed above, among a set of origins based on the expectation of how different origins' performance (e.g., Yield, etc.) distributions indicate the likelihood that their progeny will meet or exceed a certain level of performance, it can be applied to sub-processes within the doubled haploid (DH) process as well.

For instance, when a sub-process within a DH process produces more seeds from the DH lines, it must be appreciated that after being produced, for example, there may only be a finite number of greenhouse spaces in which the DH process may normally be done. The breeding value (in the vein of FIG. 2) that would be pertinent in the process is the probability distribution of the number of kernels that a given inbred would produce per plant. Based on the likelihood that a given line produces more than a set limit, for instance 180 kernels, per plant, the limited greenhouse spaces can be allocated to the different lines to improve and/or maximize the number of kernels produced while ensuring that each line has a required and/or minimum number of kernels at the end of the process.

Due to complexity involved in the resource allocation, the algorithms and computing technologies described herein are relied on in commercial uses thereof. For purposes of illustration herein, however, a simplified example is presented. In connection therewith, it is instructive to consider a case in which three greenhouse spots must be divided between two DH lines for the purposes of creating more seeds, as described above. The relevant values for the problem are as follows:

TABLE 2

| Term | Value |
| --- | --- |
| n | 3 greenhouse units (one plant per unit) |
| $\eta$ | 180 kernels per plant |
| $P_1$ | 0.3 |
| $P_2$ | 0.9 |
| $U_1$ | 0.5 |
| $U_2$ | 1.25 |
| $\xi$ | Each line must have at least one resource |
| $\lambda_1$ | 0.3 |
| $\lambda_2$ | 0.3 |
| $\lambda_3$ | 0.4 |

In general, here, the third (diversity) term would enforce a target distribution across the origins, which in this example would likely be a desired kernel number for each origin, which would have been determined through another process or analysis. To keep this example simple for purposes of illustration, this term will be simplified by setting the target distribution to "each line must have at least one resource allocated to it." With this target, the third term would go to +1*$\lambda_3$ for solutions in which one or the other line does not have resources put into it and +0 when both lines get at least one resource. Given the other values defined above, this would preclude the solutions with a non-zero third term from yielding the minimized solution, so this example can focus just on the two possible solutions in which both lines are given resources. Expanding Equation (1) for a total of two lines (N=2) yields:

$$\text{minimize}[[-\lambda_1 P_1 x_1 + \lambda_2 (P_1(1-P_1)) U_1 x_1) + \lambda_3 * 0] + [-\lambda_1 P_2 x_2 + \lambda_2 (P_2(1-P_2)) U_2 x_2) + \lambda_3 * 0]]$$

Plugging the values from Table 2 into this expanded equation for each of the two possible ways to distribute the resources will yield results for each potential solution. Minimizing the result, in this case, will mean selecting the resource allocation that yields the smaller number from this equation.

Solution 1

Line 1 gets two resources and line 2 gets one resource.

$$[-0.3*0.3*2+0.3*0.3*0.7*0.5*2+0.4*0]+[-0.3*0.9*1+0.3*0.9*0.1*1.25*1+0.4*0]=-0.353$$

Solution 2

Line 1 gets one resource and line 2 gets two resources.

$$[-0.3*0.3*1+0.3*0.3*0.7*0.5*1+0.4*0]+[-0.3*0.9*2+0.3*0.9*0.1*1.25*2+0.4*0]=-0.531$$

As can be seen above, Solution 2, in which line 1 gets one resource and line 2 gets two resources, produces the minimal solution to Equation (1). This indicates that this solution produces the higher likelihood of producing the most seed while making sure that each line is given at least one resource. Further, it can be seen that in this particular situation, even though the uncertainty around the confidence in line 2 was much higher than line 1, the large difference in its probability of success offset out the uncertainty. While the nature of this example is simplified, by necessity for illustration herein, it is still exemplary of both the impact of the methodology and its versatility (and practical applicability) in terms of the different types of plant breeding allocations to be made.

Referring still to FIG. 4, the allocation engine 110 then allocates, at 406, the DHU accordingly for the multiple selected origins in a manner consistent with the determined resource allocation. Specifically, in the example above, with regard to Table 2, the three greenhouse units are allocated as follows: one to the Line 1 and two to the Line 2. In practice, for example, where the lines are both maize plants, a plant with an 'inducer' genotype (i.e., a plant that has a relatively high likelihood of producing a haploid progeny when crossed with a diploid maize plant) is used to pollinate the silks of one progeny plant from Line 1 and two progenies from Line 2 (where each greenhouse unit is allotted one plant). The resulting haploid progeny are exposed to a mitotic inhibitor (e.g., colchicine, etc.) in order to disrupt normal cell division and cause doubling of the chromosomes in the nucleus. Thus, the resultant plants have two identical chromosomes with elite genetics.

One of skill in the art would understand that the DHU could also be allocated to create haploid plants in vivo through parthenogenesis (apomixis) or pseudogamy; or in vitro through gynogenesis and/or androgenesis. For example, in the case of *Brassica napus* and *Brassica juncea* breeding, haploid plants can be created using microspore culture, another culture, and ovary/ovule culture in order to generate subsequent doubled haploid plants. It should be further understood that the allocation or assignment of resources, consistent with the allocation determined in method 400, may be otherwise, depending on, for example, the types of resources to be allocated/assigned and the plants to be bred.

What's more, the allocation of the resources may be done by the allocation engine 110, by users associated with the determined allocation at 406 in the method 400 (e.g., breeders, etc.), or by a combination thereof. For example, the allocation engine 110 may output a report as part of the allocation in method 400, indicating the determined allocation (e.g., where the report accounts for the resources available for the allocation and the origins assigned to those allocations, etc.), after which one or more users associated with the breeding pipeline 102 may impose the determined allocation on multiple resources. In this example, the physical resources in the breeding pipeline 102 are altered and/or implemented by allocating the resources consistent with the determined allocation, thereby providing a transformation of the resources from generic to specific (i.e., each resource is implemented with the specific origin designated in the allocation). It should be appreciated that involvement of the allocation engine 110 and/or the one or more users, or combinations thereof, may be different depending on the particular type and number of resources to be allocated, the specific breeding pipeline 102, the origins selected and allocated as described herein, etc.

In view of the above, the unique systems and method described herein provide intelligent allocation of resources in breeding pipelines. In particular, resources (and use thereof), in general, may be time consuming, costly or even limited, for specific breeding pipelines (e.g., depending on the type of plants being bred in the given pipelines, etc.). Herein, however, one or more algorithms are employed, which account for probabilities of trait performance for the origins (e.g., expressed as a binomial distribution, etc.), as well as risk and/or genotypic components and/or diversity associated with the selected origins. By the described algorithm(s), resources (whether they include growing space (e.g., field plots, etc.), field equipment, lab space, lab equipment, people, etc.) (or a combination or subset thereof) are allocated with a higher likelihood of producing progenies performing above one or more thresholds and/or a higher likelihood of producing progenies expressing certain genetic components at rates deemed to be appropriate and/or desired for the breeding pipelines. The breeding pipelines, therefore, relying on data related to the origins not previously relied on to allocate resources (and by extension the process implementing the data) (i.e., using particular information and techniques), allows for the improvement described herein to be realized (i.e., improves existing technologies and processes for allocating resources to promote identified origins of greater potential into more resources) over the conventional even distribution of resources among identified origins.

With that said, it should be appreciated that the functions described herein, in some embodiments, may be described in computer executable instructions stored on a computer readable media, and executable by one or more processors. The computer readable media is a non-transitory computer readable media. By way of example, and not limitation, such computer readable media can include RAM, ROM, EEPROM, CD-ROM or other optical disk storage, magnetic disk storage or other magnetic storage device, or any other medium that can be used to carry or store desired program code in the form of instructions or data structures and that can be accessed by a computer. Combinations of the above should also be included within the scope of computer-readable media.

It should also be appreciated that one or more aspects of the present disclosure transform a general-purpose computing device into a special-purpose computing device when configured to perform the functions, methods, and/or processes described herein.

As will be further appreciated based on the foregoing specification, the above-described embodiments of the disclosure may be implemented using computer programming or engineering techniques, including computer software, firmware, hardware or any combination or subset thereof, wherein the technical effect may be achieved by performing at least one of the following operations: (a) for multiple origins, accessing a data structure including data representative of the multiple origins, the data including, for each of the multiple origins, a trait performance expression and/or genotypic components; (b) determining, by at least one computing device, a resource allocation, which allocates n resources among the multiple origins, based on a probability associated with the trait performance expressions and/or genotypic components for the origins, wherein n is an integer; and (c) allocating the n resources in a breeding pipeline for the multiple origins, based on the determined resource allocation, whereby the origins are imposed on the resources consistent with the resources allocation; and/or (d) Wherein: (i) determining the resource allocation includes determining the resource allocation based on a comparison of:

$$\text{value} \sum_{i=1}^{N} -\lambda_1 \mathbb{P}(\theta_i > \eta) x_i + \lambda_2 [\mathbb{P}(\theta_i > \eta)(1 - \mathbb{P}(\theta_i > \eta)) U_i x_i] + \lambda_3 \|TI_H x - \xi\|_1$$

for multiple potential resource allocations; (ii) at least one of the n resources is allocated in the resource allocation to each of the multiple origins; and wherein each of the n resources is allocated in the resource allocation to one of the multiple origins; (iii) determining the resource allocation for a hybrid crop in which male and female heterotic pools are kept separate includes determining the resource allocation, subject to:

$M^T y \geq m\alpha_M$, $F^T y \geq m\alpha_F$, and $\alpha_M + \alpha_F \geq A1$;

(iv) determining the resource allocation includes determining the resource allocation based on a predefined target portfolio, whereby a relative value for each potential resource allocation is diminished based on a deviation of the resource allocation from the predefined target portfolio; and/or (v) determining the resource allocation includes determining the resource allocation based on a confidence in the trait performance expression and/or the genotypic components for each of the multiple origins.

Examples and embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. In addition, advantages and improvements that may be achieved with one or more exemplary embodiments disclosed herein may provide all or none of the above mentioned advantages and improvements and still fall within the scope of the present disclosure.

Specific values disclosed herein are example in nature and do not limit the scope of the present disclosure. The disclosure herein of particular values and particular ranges of values for given parameters are not exclusive of other values and ranges of values that may be useful in one or more of the examples disclosed herein. Moreover, it is envisioned that any two particular values for a specific parameter stated herein may define the endpoints of a range of values that may also be suitable for the given parameter (i.e., the disclosure of a first value and a second value for a given parameter can be interpreted as disclosing that any value between the first and second values could also be employed for the given parameter). For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When a feature is referred to as being "on," "engaged to," "connected to," "coupled to," "associated with," "in communication with," or "included with" another element or layer, it may be directly on, engaged, connected or coupled to, or associated or in communication or included with the other feature, or intervening features may be present. As used herein, the term "and/or" and "at least one of" includes any and all combinations of one or more of the associated listed items.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

Although the terms first, second, third, etc. may be used herein to describe various features, these features should not be limited by these terms. These terms may be only used to distinguish one feature from another. Terms such as "first," "second," and other numerical terms when used herein do not imply a sequence or order unless clearly indicated by the context. Thus, a first feature discussed herein could be termed a second feature without departing from the teachings of the example embodiments.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A computer-implemented method for allocating resources in a breeding pipeline to multiple origins, the method comprising:
   for multiple origins, accessing a data structure including data representative of the multiple origins, the data including, for each of the multiple origins, a trait performance expression and/or genotypic components;
   determining, by at least one computing device, a resource allocation, which allocates n resources among the multiple origins, based on: (i) a probability associated with the trait performance expressions and/or genotypic components for the origins, and (ii) a predefined target portfolio, wherein n is an integer, and whereby a relative value for each potential resource allocation is diminished based on a deviation of the resource allocation from the predefined target portfolio; and
   allocating the n resources in a breeding pipeline for the multiple origins, based on the determined resource allocation.

2. The c method of claim 1, wherein determining the resource allocation includes determining the resource allocation based on a comparison of:

$$\text{value} \sum_{i=1}^{N} - \lambda_1 \mathbb{P}(\theta_i > \eta) x_i + \lambda_2 [\mathbb{P}(\theta_i > \eta)(1 - \mathbb{P}(\theta_i > \eta)) U_i x_i] + \lambda_3 \|TI_H x - \xi\|_1$$

for multiple potential resource allocations;
   wherein N is a number of the potential allocations; $\lambda_1$, $\lambda_2$, and $\lambda_3$ are weighting variables, $\eta$ is a target threshold for breeding value; $\theta_i$ is a variable for a breeding value, or a vector thereof, for the specific origin; $\mathbb{P}$ is the probability of finding a breeding value, or a vector thereof, larger than some threshold for the specific origin; $U_i$ is a confidence level of genetic learning for a specific origin; T is a transition probability matrix; $I_H$ is an incidence matrix for mapping heterotic pools; x is a selected one of the multiple origins; $\xi$ is a target portfolio of breeding objectives; and $x_i$ is an integer decision variable for resources allocated to the specific origin.

3. The method of claim 2, wherein at least one of the n resources is allocated in the resource allocation to each of the multiple origins;
   wherein each of the n resources is allocated in the resource allocation to one of the multiple origins;
   wherein determining the resource allocation for a hybrid crop in which male and female heterotic pools are kept separate includes determining the resource allocation, subject to:

$$M^T y \geq m\alpha_M,$$

$$F^T y \geq M\alpha_F,$$

and $$\alpha_M + \alpha_F \leq 1;$$

wherein M is the male incidence vector; $\alpha_M$ is the minimum fraction of m origins that are designated to be devoted to male crosses; F is the female incidence vector; T is a transition probability matrix; y is the binary selection variable that indicates which of the multiple origins have been selected; and $\alpha_F$ is the minimum fraction of m origins that are designated to be devoted to female crosses; and
whereby the n resources are able to be properly allocated to each heterotic pool without exceeding the maximum m origins.

4. The method of claim 1, wherein at least one of the n resources is allocated in the resource allocation to each of the multiple origins; and wherein each of the n resources is allocated in the resource allocation to one of the multiple origins.

5. The method of claim 4, wherein determining the resource allocation for a hybrid crop in which male and female heterotic pools are kept separate includes determining the resource allocation, subject to:

$$M^T y \geq m\alpha_M,$$

$$F^T y \geq M\alpha_F,$$

and $$\alpha_M + \alpha_F \leq 1;$$

wherein M is the male incidence vector; $\alpha_M$ is the minimum fraction of m origins that are designated to be devoted to male crosses; F is the female incidence vector; T is a transition probability matrix; y is the binary selection variable that indicates which of the multiple origins have been selected; and $\alpha_F$ is the minimum fraction of m origins that are designated to be devoted to female crosses; and
whereby the n resources are able to be properly allocated to each heterotic pool without exceeding the maximum m origins.

6. The method of claim 1, wherein determining the resource allocation includes determining the resource allocation based on a confidence in the trait performance expression and/or the genotypic components for each of the multiple origins.

7. The method of claim 1, further comprising planting a plant product based on at least one of the multiple origins and at least one progeny from the multiple origins.

8. A system for allocating resources in a breeding pipeline, the system comprising:
   a data structure including data representative of multiple selected origins, the data including a trait performance expression and/or genotypic components for each of the multiple selected origins; and
   a computing device coupled in communication with the data structure and configured to:
      access data in the data structure for each of the multiple selected origins; and
      determine a resource allocation, which allocates n resources among the multiple selected origins, based on (i) a probability associated with the trait performance expression and/or the genotypic components for the origins, and (ii) a predefined target portfolio, wherein n is an integer, and whereby a relative value for each potential resource allocation is diminished based on a deviation of the resource allocation from the predefined target portfolio.

9. The system of claim 8, further comprising a breeding pipeline; and
wherein the breeding pipeline includes the N resources allocated consistent with said determined resource allocation.

10. The system of claim 9, wherein the computing device is configured to determine the resource allocation based on a reduction and/or minimization of the value for each potential allocation, wherein the value for each potential allocation is defined as:

$$\text{value} \sum_{i=1}^{N} -\lambda_1 \mathbb{P}(\theta_i > \eta) x_i + \lambda_2 [\mathbb{P}(\theta_i > \eta)(1 - \mathbb{P}(\theta_i > \eta)) U_i x_i] + \lambda_3 \|TI_H x - \xi\|_1$$

wherein N is a number of potential allocations; $\lambda_1$, $\lambda_2$, and $\lambda_3$ are weighting variables; $\eta$ is a target threshold for a breeding value; $\theta_i$ is a variable for a breeding value, or a vector thereof, for the specific origin; $\mathbb{P}$ is the probability of finding a breeding value, or a vector thereof, larger than some threshold for the specific origin; $U_i$ is a confidence level of genetic learning for a specific origin; T is a transition probability matrix; $I_H$ is an incidence matrix for mapping heterotic groups to the multiple origins; x is a selected one of the multiple origins; $\xi$ is a target portfolio of breeding objectives; and $x_i$ is an integer decision variable for resources allocated to the specific origin.

11. The system of claim 10, wherein at least one of the n resources is allocated, in the resource allocation, to each of the multiple origins; and wherein each of the n resources is allocated, in the resource allocation, to one of the multiple origins.

12. The system of claim 10, wherein the computing device is configured to determine the resources allocation further consistent with:

$1^T x = n;$ $1^T y = m;$ $M^T y \geq m\alpha_M;$ $F^T y \geq m\alpha_F;$ $I_p y \leq m\alpha_y$ $u_{lower} \leq x \leq u_{upper};$ $x/u_{upper} \leq y \leq x;$ $x \in \mathbb{Z}_+;$ and $y \in \{0,1\};$ wherein x is the integer resource allocation variable that indicates the resources allocated to each origin; n is the total number of resources available to allocate; y is the binary selection variable that indicates which origins have been selected; m is the target number of origins in the selected set; M is the male incidence vector; $\alpha_M$ is the minimum fraction of m origins that are designated to be devoted to male crosses; F is the female incidence vector; $\alpha_F$ is the minimum fraction of f origins that are designated to be devoted to female crosses; $I_p$ is the parent incidence vector for origins; $\alpha_p$ is the threshold set for maximum rate of parental use within the selected set; $u_{lower}$ is the lower bound of the number of resources that can be allocated to the i-th origin; $u_{upper}$ is the upper bound of the number of resources that can be allocated to the i-th origin; and $\mathbb{Z}_+$ is a set of positive integers.

13. The system of claim 8, wherein the computing device is configured to determine the resource allocation based on a reduction and/or minimization of the value for each potential allocation, wherein the value for each potential allocation is defined as:

$$\text{value} \sum_{i=1}^{N} -\lambda_1 \mathbb{P}(\theta_i > \eta) x_i + \lambda_2 [\mathbb{P}(\theta_i > \eta)(1 - \mathbb{P}(\theta_i > \eta)) U_i x_i] + \lambda_3 \|TI_H x - \xi\|_1$$

wherein N is a number of potential allocations; $\lambda_1$, $\lambda_2$, and $\lambda_3$ are weighting variables; n is a target threshold for a breeding value; $\theta_i$ is a variable for a breeding value, or a vector thereof, for the specific origin; $\mathbb{P}$ is the probability of finding a breeding value, or a vector thereof, larger than some threshold for the specific origin; $U_i$ is a confidence level of genetic learning for a specific origin; T is a transition probability matrix; $I_H$ is an incidence matrix for mapping heterotic groups to the multiple origins; x is a selected one of the multiple origins; $\xi$ is a target portfolio of breeding objectives; and $x_i$ is an integer decision variable for resources allocated to the specific origin.

14. The system of claim 8, wherein at least one of the n resources is allocated, in the resource allocation, to each of the multiple origins; and wherein each of the n resources is allocated, in the resource allocation, to one of the multiple origins.

15. The system of claim 8, wherein the computing device is configured to determine the resources allocation further consistent with:

$1^T x = n;$ $1^T y = m;$ $M^T y \geq m\alpha_M;$ $F^T y \geq m\alpha_F;$ $I_p y \leq m\alpha_y$ $u_{lower} \leq x \leq u_{upper};$ $x/u_{upper} \leq y \leq x;$ $x \in \mathbb{Z}_+;$ and $y \in \{0,1\};$ wherein x is the integer resource allocation variable that indicates the resources allocated to each origin; n is the total number of resources available to allocate; y is the binary selection variable that indicates which origins have been selected; m is the target number of origins in the selected set; M is the male incidence vector; $\alpha_M$ is the minimum fraction of m origins that are designated to be devoted to male crosses; F is the female incidence vector; $\alpha_F$ is the minimum fraction of f origins that are designated to be devoted to female crosses; $I_p$ is the parent incidence vector for origins; $\alpha_p$ is the threshold set for maximum rate of parental use within the selected set; $u_{lower}$ is the lower bound of the number of resources that can be allocated to the i-th origin; $u_{upper}$ is the upper bound of the number of resources that can be allocated to the i-th origin; and $\mathbb{Z}_+$ is a set of positive integers.

16. A computer-implemented method for allocating resources in a breeding pipeline to multiple origins, the method comprising:

for multiple origins, accessing a data structure including data representative of the multiple origins, the data including, for each of the multiple origins, a trait performance expression and/or genotypic components;

determining, by at least one computing device, a resource allocation, which allocates n resources among the multiple origins, based on: (i) a probability associated with the trait performance expressions and/or genotypic components for the origins, and (ii) a predefined target portfolio, wherein n is an integer, and whereby a relative value for each potential resource allocation is diminished based on a deviation of the resource allocation from the predefined target portfolio;

allocating the n resources in a breeding pipeline for the multiple origins, based on the determined resource allocation; and planting a plant product based on at least one of the multiple origins and at least one progeny from the multiple origins.

17. The method of claim 16, wherein determining the resource allocation includes determining the resource allocation based on a comparison of:

$$\text{value} \sum\nolimits_{i=1}^{N} -\lambda_1 \mathbb{P}(\theta_i > \eta) x_i + \lambda_2 [\mathbb{P}(\theta_i > \eta)(1 - \mathbb{P}(\theta_i > \eta)) U_i x_i] + \lambda_3 \| TI_H x - \xi \|_1$$

for multiple potential resource allocations;

wherein N is a number of the potential allocations; $\lambda_1$, $\lambda_2$, and $\lambda_3$ are weighting variables; $\eta$ is a target threshold for breeding value; $\theta_i$ is a variable for a breeding value, or a vector thereof, for the specific origin; $\mathbb{P}$ is the probability of finding a breeding value, or a vector thereof, larger than some threshold for the specific origin; $U_i$ is a confidence level of genetic learning for a specific origin; T is a transition probability matrix; $I_H$ is an incidence matrix for mapping heterotic groups to the multiple origins; x is a selected one of the multiple origins; $\xi$ is a target portfolio of breeding objectives; and $x_i$ is an integer decision variable for resources allocated to the specific origin.

18. The method of claim 17, wherein at least one of the n resources is allocated in the resource allocation to each of the multiple origins;

wherein each of the n resources is allocated in the resource allocation to one of the multiple origins;

wherein determining the resource allocation for a hybrid crop in which male and female heterotic pools are kept separate includes determining the resource allocation, subject to:

$M^T y \geq m \alpha_M$, $F^T y \geq M \alpha_F$, and $\alpha_M + \alpha_F \leq 1$;

wherein M is the male incidence vector; $\alpha_M$ is the minimum fraction of m origins that are designated to be devoted to male crosses; F is the female incidence vector; v is the binary selection variable that indicates which origins have been selected; and $\alpha_F$ is the minimum fraction of m origins that are designated to be devoted to female crosses; and whereby the n resources are able to be properly allocated to each heterotic pool without exceeding the maximum m origins.

19. The method of claim 16, wherein at least one of the n resources is allocated in the resource allocation to each of the multiple origins; and wherein each of the n resources is allocated in the resource allocation to one of the multiple origins.

20. The method of claim 19, wherein determining the resource allocation for a hybrid crop in which male and female heterotic pools are kept separate includes determining the resource allocation, subject to:

$M^T y \geq m \alpha_M$, $F^T y \geq M \alpha_F$, and $\alpha_M + \alpha_F \leq 1$;

wherein M is the male incidence vector; $\alpha_M$ is the minimum fraction of m origins that are designated to be devoted to male crosses; F is the female incidence vector; T is a transition probability matrix; y is the binary selection variable that indicates which origins have been selected; and $\alpha_F$ is the minimum fraction of m origins that are designated to be devoted to female crosses; and whereby the n resources are able to be properly allocated to each heterotic pool without exceeding the maximum m origins.

21. The method of claim 16, wherein determining the resource allocation includes determining the resource allocation based on a predefined target portfolio, whereby a relative value for each potential resource allocation is diminished based on a deviation of the resource allocation from the predefined target portfolio.

22. The method of claim 16, wherein determining the resource allocation includes determining the resource allocation based on a confidence in the trait performance expression and/or the genotypic components for each of the multiple origins.

* * * * *